United States Patent
Pan et al.

(10) Patent No.: US 10,603,168 B2
(45) Date of Patent: Mar. 31, 2020

(54) VALVE CLAMP

(71) Applicant: Zhongshan Hospital, Fudan University, Shanghai (CN)

(72) Inventors: Wenzhi Pan, Shanghai (CN); Daxin Zhou, Shanghai (CN); Junbo Ge, Shanghai (CN); Leilei Cheng, Shanghai (CN)

(73) Assignee: ZHONGSHAN HOSPITAL, FUDAN UNIVERSITY, Shanghai (CN)

( * ) Notice: Subject to any disclaimer, the term of this patent is extended or adjusted under 35 U.S.C. 154(b) by 330 days.

(21) Appl. No.: 15/736,298

(22) PCT Filed: Feb. 15, 2017

(86) PCT No.: PCT/CN2017/073563
§ 371 (c)(1),
(2) Date: Dec. 14, 2017

(87) PCT Pub. No.: WO2018/018873
PCT Pub. Date: Feb. 1, 2018

(65) Prior Publication Data
US 2019/0000623 A1    Jan. 3, 2019

(30) Foreign Application Priority Data

Jul. 26, 2016 (CN) .......................... 2016 1 0594219

(51) Int. Cl.
*A61F 2/24* (2006.01)
*A61B 17/00* (2006.01)
(Continued)

(52) U.S. Cl.
CPC ............ *A61F 2/2454* (2013.01); *A61B 17/00* (2013.01); *A61B 17/122* (2013.01);
(Continued)

(58) Field of Classification Search
CPC ...... A61F 2/2454; A61F 2/246; A61F 2/2466; A61F 2220/0033; A61F 2230/0054;
(Continued)

(56) References Cited

U.S. PATENT DOCUMENTS 5,350,399 A * 9/1994 Erlebacher .......... A61B 17/0057
128/899
6,508,828 B1 * 1/2003 Akerfeldt ........... A61B 17/0057
606/215
(Continued)

FOREIGN PATENT DOCUMENTS

| CN | 102860846 A | 1/2013 |
| CN | 202859228 U | 4/2013 |

(Continued)

*Primary Examiner* — Phong Son H Dang
(74) *Attorney, Agent, or Firm* — Bayramoglu Law Offices LLC

(57) ABSTRACT

A valve clamp for treating the cardiac valve regurgitation. The valve clamp includes a first clamp part, a second clamp part, and a connecting part. The first clamp part has the first clamping arms. The second clamp part has a corresponding number of second clamping arms. The first clamping arm and the second clamping arm can clip an object therebetween through the interaction force generated by closing and pushing against each other. Moreover, the valve clamp can also include a closed ring, which is sleeved outside the periphery of the first clamp part and the periphery of the second clamp part, such that the clamping arms can close as needed, and the clamping is tighter. The valve clamp has the advantages of a minimally invasive implantation, a simple manufacture, a low difficulty of operation, good effects, etc.

7 Claims, 9 Drawing Sheets

(51) Int. Cl.
*A61B 17/128* (2006.01)
*A61B 17/122* (2006.01)

(52) U.S. Cl.
CPC ......... *A61B 17/1285* (2013.01); *A61F 2/246* (2013.01); *A61F 2/2466* (2013.01); *A61B 2017/00243* (2013.01); *A61F 2220/0008* (2013.01); *A61F 2220/0033* (2013.01); *A61F 2230/0054* (2013.01)

(58) Field of Classification Search
CPC .......... A61F 2220/0008; A61B 17/122; A61B 17/00; A61B 17/1285; A61B 2017/00243
See application file for complete search history.

(56) References Cited

U.S. PATENT DOCUMENTS

| | | | |
|---|---|---|---|
| 7,604,646 B2 * | 10/2009 | Goldfarb | A61B 17/00234 606/151 |
| 8,398,676 B2 * | 3/2013 | Roorda | A61B 17/0057 606/213 |
| 10,130,475 B1 * | 11/2018 | Metchik | A61F 2/2466 |
| 10,231,837 B1 * | 3/2019 | Metchik | A61F 2/246 |
| 2003/0153946 A1 | 8/2003 | Kimblad | |
| 2006/0009800 A1 * | 1/2006 | Christianson | A61B 17/0057 606/213 |
| 2006/0020275 A1 | 1/2006 | Goldfarb et al. | |
| 2010/0022823 A1 * | 1/2010 | Goldfarb | A61B 17/0401 600/37 |
| 2012/0109161 A1 * | 5/2012 | Privitera | A61B 34/30 606/142 |
| 2016/0174979 A1 * | 6/2016 | Wei | A61B 17/1285 606/151 |
| 2019/0142589 A1 * | 5/2019 | Basude | A61B 17/1227 623/2.11 |
| 2019/0261995 A1 * | 8/2019 | Goldfarb | A61B 17/0469 |
| 2019/0343630 A1 * | 11/2019 | Kizuka | A61F 2/2466 |

FOREIGN PATENT DOCUMENTS

| | | |
|---|---|---|
| WO | 03001893 A2 | 1/2003 |
| WO | 2014182849 A1 | 11/2014 |
| WO | 2016040526 A1 | 3/2016 |

* cited by examiner

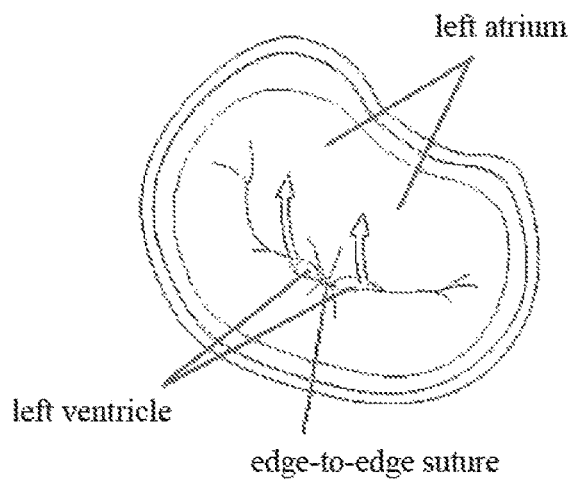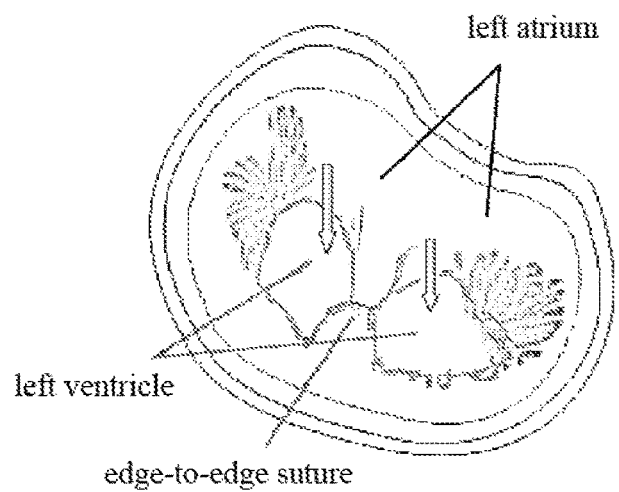
Figure 2a
Figure 2b

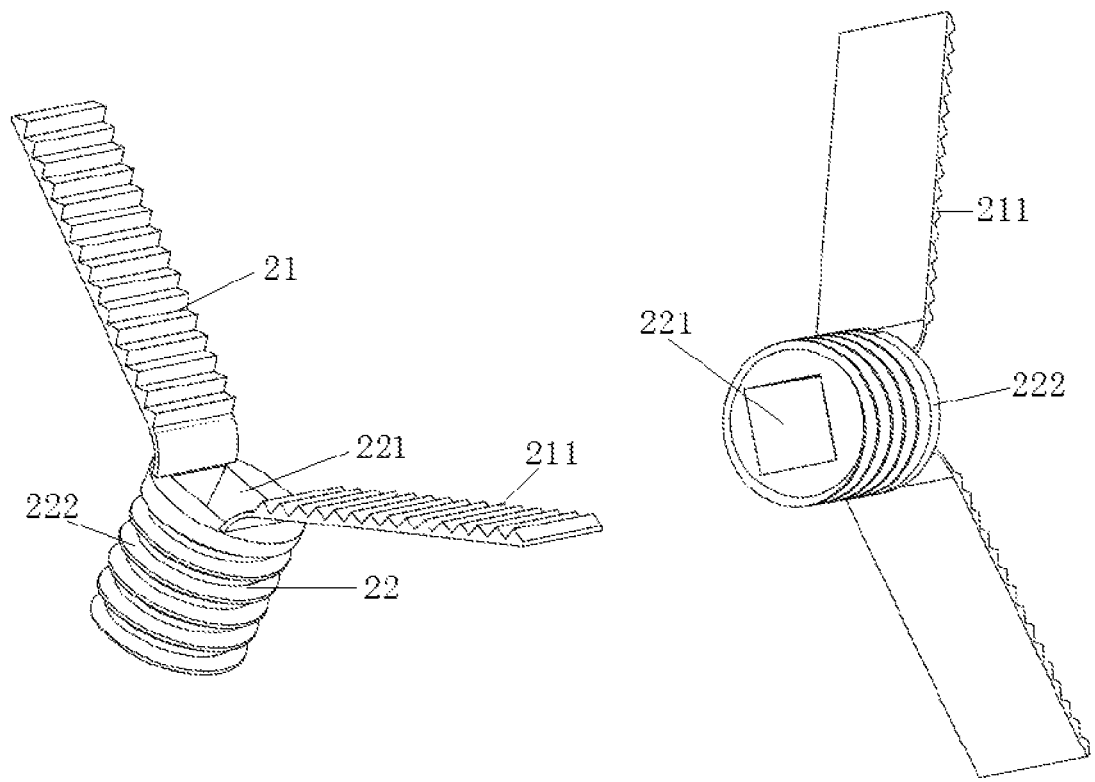
Figure 7a                           Figure 7b

VALVE CLAMP

CROSS REFERENCE TO RELATED APPLICATIONS

This application is the national phase of International Application No. PCT/CN2017/073563, filed on Feb. 15, 2017, which is based upon and claims priority to Chinese Patent Application No. 201610594219.8, filed on Jul. 26, 2016 the entire contents of which are incorporated herein by reference.

TECHNICAL FIELD

The present invention relates to a valve clamp, particularly to a valve clamp which is used to treat the cardiac valve regurgitation.

BACKGROUND OF THE INVENTION

The mitral valves are two pieces of valves attached to the periphery of the left atrioventricular orifice (as shown in FIG. 1), connecting to the papillary muscles through the chordaetendineae, and functioning to prevent the blood in the left ventricle from flowing back to the left atrium.

Mitral valve regurgitation (MR) is caused by organic or functional lesion of the mitral valve leaflets and associated structures, leading to it insufficient coaptation of the anterior and posterior leaflets of the mitral valve. As a result, the blood flows back from the left ventricle to the left atrium, causing a series of pathological and physiological changes. Serious MR will lead to left ventricle enlargement, impair the systolic function of the left heart, and finally cause a heart failure. Meanwhile, the pressure of the left atrium also increases due to the regurgitation, easily causing the enlargement of the left atrium, atrial fibrillation, and pulmonary artery hypertension. The prognosis of the MR is poor. The annular mortality rate of patients who have the symptoms but do not undergo surgery is about 5%. Moreover, the five years mortality rate of patients complicated with serious heart failure is up to 60%. Meanwhile, the MR is also one of the most common heart diseases. According to the statistics, the prevalence rate of MR among the people who are over 65 and over 75 years old are 6.4% and 9.3% respectively. With the development of the economy and the society and the aging of the population, this rate shows a significantly rising trend.

Clinical trials show that the drug therapy can only relieve the symptom of the patients, without extending the survival period of the patients or providing operation time. Surgical valve repair or replacement operations are deemed as the standard treatment of the disease, and has been proven to be effective to relieve the symptom and prolong the life of the patients. However, the operation has the deficiencies such as serious trauma, heavy postoperative pain, slow recovery, high risk, and so on. Furthermore, patients with advanced age, thoracotomy history, poor cardiac function, or along with multiple organ dysfuntions, are usually refused to be operated on due to the high risk of the operation. Thus, developing a minimally invasive and low risk treatment device to treat the MR has the significant social benefit and can meet the market demand. Recently, with the breakthrough development of the interventional treatment technology for heart valves, the MR interventional device has currently become one of the focused directions of the research on the cardiovascular device, both domestically and overseas.

The valve clamp or clamp devices developed based on the technical principle of the surgical edge-to-edge suture of the valve is currently most recognized due to high safety, simple technical principle, and high feasibility. The technical principle of the surgical edge-to-edge suture of the valve is shown in FIGS. 2a and 2b. When the mitral valve regurgitation occurs, during the cardiac systolic period, edges of the two leaflets of the valve cannot close sufficiently, leaving a gap between them. As a result, the blood in the left ventricle flows back from the gap to the left atrium. Surgical edge-to-edge suture technique is to suture the intermediate points on the edges of the two leaflets of the mitral valve. Thus, during the cardiac systolic period, the gap between the leaflets of the valve is changed from one big hole into two small holes, so as to reduce the mitral valve regurgitation (FIG. 2a). Moreover, during the cardiac diastolic period, the blood flowing into the left ventricle, while the opening of mitral valve is not affected (FIG. 2b). The only minimally invasive interventional device for treating MR, which is approved and available on the market internationally, is MitraClip manufactured by Evalve corporation, and is a valve clamping device. However, MitraClip has a complex operating system, and high manufacturing cost. During the procedure, the device needs to go through the vein, the right atrium, the atrial septum, the left atrium, and finally reach the left ventricle. The access path is long with many turning points. Thus, the procedure is complex. The operators need to repeatedly and finely adjust the bends, the direction, the horizontal position, and the vertical depth of the delivery system until an ideal location is reached to clip the valve. Thus, the operators usually need to spend a lot of time to finish an operation, which is a drawback resulting in a lot of criticism.

Currently, in China, there is no MR device available in the market or under clinical trials. Thus, developing the interventional device for MR has the significance. Even though the Chinese patent application number CN102860846A discloses an edge-to-edge clamping device, the device is used for the tricuspid valve regurgitation, and cannot be used to treat the mitral valve regurgitation. Additionally, when the device is clipping the leaflets of the valve, the leaflets of the valve are not further clipped to close toward the central line, leaving a gap between the leaflets. Thus, the blood can flow through the gap. Accordingly, the efficacy of the operation is reduced greatly.

Thus, persons of ordinary skill in the art are making efforts to develop an interventional device for MR with a low cost, easy operation, and ideal effect.

SUMMARY OF THE INVENTION

In view of the above defects in the surgical techniques, the technical problem to be solved by the present invention is how to use the minimally invasive intervention method to treat the MR safely and effectively.

In order to achieve the above objectives, the present invention provides a valve clamp for treating the MR. The clamp can be implanted through a minimally invasive path, treating the MR effectively.

The valve clamp includes the first clamp part, the second clamp part, and the connecting part. The first clamp part includes at least two first clamping arms. The second clamp part includes second clamping arms corresponding to the first clamping arms. Each first clamping arm and each corresponding second clamping arm can form a group of clamp. Each first clamping arm and each corresponding second clamping arm clamp an object therebetween through the interaction force generated by closing up and pushing against each other. The connecting part is used to connect the first clamp part and the second clamp part.

Furthermore, the first clamping arm inclines toward the front of the clamp. The second clamping arm also inclines toward the front of the clamp. However, an inclined angle of the second clamping arm is more than that of the first clamping arm, wherein the inclined angle of the first clamping arm is 20-30°, and the inclined angle of the second clamping arm is 25-35°. While the clamp is in use, the first clamping arm and the second clamping arm close up from both sides of the valve respectively, so as to perform the role of clipping the valve.

Preferably, there are two or three first clamping arms. Correspondingly, there are two or three second clamping arms, i.e., the number of groups of the clamps is two or three. The embodiment with two groups of clamps corresponds to the mitral valve. The embodiment with three groups of clamps corresponds to the tricuspid valve. Moreover, more or less clamping arms can also be provided according to the actual condition.

Preferably, the length of the first clamping arm and the length of the second clamping arm are respectively 4.0-8.0 mm, optimally 6.0 mm.

In one preferred embodiment of the present invention, the valve clamp has a pair of first clamping arms and a pair of corresponding second clamping arms symmetrically. Furthermore, the pair of first clamping arms is V-shaped forward. The included angle of the pair of first clamping arms is 120-140°, optimally 130°. The pair of second clamping arms is also V-shaped forward. The included angle of the pair of second clamping arms is slightly less than the included angle of the pair of first clamping arms. The included angle of the pair of second clamping arms is 110-130°, optimally 120°.

Preferably, a surface of the first clamping arm, and an opposite surface of the second clamping arm both have a plurality of projections, such that the friction between the clamping arm and the valve tissue can be enhanced, preventing the clamped valve tissue from slipping out. In one preferred embodiment of the present invention, the projections are zigzag or wavy. Moreover, the pattern of ripples or waves between opposite surfaces of the clamping arms engage with each other. In another preferred embodiment of the present invention, the projections are thorns, which can pierce into the valve tissue, so as to improve the property of the clamping arm to clip the valve.

Furthermore, the connecting part includes a locking bar and a clamping ring fitting each other. The first clamp part and the second clamp part are separately provided on the locking bar or the clamping ring, i.e., the first clamp part and the second clamp part are respectively connected to the locking bar or the clamping ring. The locking bar is inserted into a ring hole of the clamping ring so as to achieve a connection of the first clamp part and the second clamp part. Also, a locking part is further provided between the locking bar and the clamping ring. The locking part not only can lock the connection between the locking bar and the clamping ring, but also can lock the clamping state of the first clamping arm and the second clamping arm.

Furthermore, the locking part has operational reversibility. When the clamping result is not good enough, the locking bar and the clamping ring can be separated, so as to retrieve the valve clamp.

In one embodiment of the present invention, the first clamp part is provided on the locking bar. The second clamp part is provided on the clamping ring. In another embodiment of the present invention, the first clamp part is provided on the clamping ring. The second clamp part is provided on the locking bar.

Preferably, the axial length of the locking bar is 5.0-8.0 mm. The outer diameter of the clamping ring is 4.0-6.0 mm. The axial length of the clamping ring is 3.0-5.0 mm.

In one preferred embodiment of the present invention, the first clamp part includes the locking bar and a plurality of first clamping arms. The plurality of the first clamping arms extends outward with the locking bar as the center. The second clamp part includes the clamping ring and a plurality of the second clamping arms. The plurality of the second clamping arms extends outward with the clamping ring as the center.

In one embodiment of the present invention, the locking part is provided on the locking bar. The locking part can be an elastic piece or a spring convex button. The locking part can also be the elastic polymer material surrounding and fixed to the periphery of the locking bar. In another embodiment of the present invention, the locking part includes a spring convex button provided on the locking bar and a groove provided on the clamping ring.

Preferably, the locking part has operational reversibility. For example, if the elastic piece is used, the clamping ring can pass over the elastic piece on the locking bar. The elastic piece can obliquely support the clamping ring, preventing the clamping ring from being retracted, such that the clamping ring is fixed. However, if the force for being retracted increases, the clamping ring can still reversely pass over the elastic piece, so as to separate the clamping ring from the locking bar. Thus, when the clamping result is not good enough, the combined first clamp part and the second clamp part can be detached, and the valve clamp can be retrieved.

Furthermore, in order to avoid the rotational displacement of the locking bar with respect to the clamping ring, the locking bar is configured to be in a shape of a square column. Accordingly, the ring hole of the clamping ring is configured to be a corresponding hole in the shape of a square column. The side length of the cross-section of the square column is preferably 1.5-2.5 mm.

Furthermore, the rear end of the locking bar is provided with a connecting port, which is used to connect to the delivery device. Preferably, the connecting manner of connecting the connecting port to the delivery device is a threaded connection, i.e., the inside of the connecting port is provided with the internal thread, while the deliver rod used for delivering is provided with the external thread.

Furthermore, the first clamping arm and the second clamping arm both have the following forms, i.e., the first form of completely radially contracting, the second form of completely radially expanding, and the third form of half contracting and half expanding (under the clamping status). The first form is the one in which the clamp is delivered through the catheter. The second form is the one in which the clamp is released from the delivery sheath. The third form is the working form after the clamp clamps the valve tissue.

Preferably, the valve clamp is made of the material with high supporting strength, and is particularly made of the elastic alloy material with strong resilience, such as Ni—Ti alloy.

Preferably, the closed ring is sleeved outside a periphery of the first clamp part and a periphery of the second clamp part, such that the first clamping arm and the second clamping arm can close as per need, and the clamping is tighter.

Preferably, the axial length of the closed ring is 5.0-9.0 mm. The inner diameter of the closed ring is 4.0-6.0 mm. The outer diameter of the closed ring is 4.5-7.0 mm.

Furthermore, an internal surface of the closed ring is provided with an internal. thread. An external surface of the clamping ring is provided with an external thread. The internal thread fits the external thread, such that the closed ring and the clamping ring can be bonded to each other tightly. Moreover, the relative position of the closed ring with respect to the clamping ring can be adjusted freely. After the clamping ring is screwed into the closed ring completely, the closed ring can play the role of closing and shutting up the first and the second clamping arms toward the central line. Thus, the property of the clamping arm to clip the valve tissue can be further improved. Also, the held valve tissue can be clamped and closed towards the middle.

The present invention also provides a delivery device of the valve clamp. The delivery device includes a delivery rod, a delivery pipe, and a delivery sheath. The delivery rod can be connected to the locking bar. The delivery rod is used to deliver the first or the second clamp part which is provided on the locking bar. The delivery pipe can be connected to the clamping ring. The delivery pipe is used to deliver the second or the first clamp part which is provided on the clamping ring. The delivery sheath is used to enclose the valve clamp and at the same time to provide the delivery trail. The delivery rod is located in the innermost layer. The delivery pipe is located in the intermediate layer. The delivery sheath is located in the outermost layer.

Preferably, the diameter of the delivery rod is 1.2-2.0 mm. The inner diameter of the delivery pipe is 4.0-6.0 mm. The outer diameter of the delivery pipe is 4.5-7.0 mm. The inner diameter of the delivery sheath is 4.5-7.0 mm. The outer diameter of the delivery sheath is 5.0-7.5 mm.

Preferably, the front end of the delivery rod is provided with an external thread, which is used to connect to the internal thread of the locking bar, so as to achieve the delivery of the first or the second clamp part provided on the locking bar.

Preferably, the front end of the delivery pipe is provided with the closed ring connecting part, such that the closed ring can be detachably connected to the delivery pipe. Moreover, the closed ring can be connected to the clamping ring via the thread, such that the delivery of the second or the first clamp part provided on the clamping ring is achieved. The closed ring connecting part can be a thread, a snap-in joint, a snap-in groove, a stitching, etc.

In one preferred embodiment of the present invention, the annular wall at the rear end of the closed ring is provided with 3-4 small holes along the axis. The tubal wall at the front end of the delivery pipe is provided with 3-4 nails along the axis. The nails can be inserted into the small holes, such that the closed ring and the delivery pipe can be combined. When the delivery pipe is driven forward or rotated, the closed ring will move forward or rotate accordingly. When the delivery pipe moves backward, the closed ring and the delivery pipe can be separated.

Furthermore, in order to reinforce the combination of the closed ring and the delivery pipe, a suture line can be provided therebetween. The suture line can extend outside the body. When the clamping reaches a satisfied working state, the suture line can be cut off outside the body, such that the closed ring and the delivery pipe can be separated.

In the context, the term "the front end" refers to the end which is away from the operator after the valve clamp is delivered into the body. In the context, the term "the rear end" refers to the end which is near the operator after the valve clamp is delivered into the body. Moreover, in the context, the terms "front" and "forward" refer to the direction which is away from the operator along the delivery axis. In the context, the terms "rear" and "backward" refer to the direction which is near the operator along the delivery axis.

In the present invention, the surgical implantation manner of the valve clamp is to puncture the apex cordis, and feed the delivery sheath to directly reach the vicinity of the mitral valve. Here, the delivery sheath is designed to be in a shape of a straight line. Another plan is to puncture the femoral artery, and feed the delivery sheath retrogradely from the femoral artery to the ascending aorta, traveling through the aortic valve to reach the vicinity of the mitral valve. Here, the delivery sheath is designed to have a J-shaped front end which can turn around.

The present invention is used to treat the mitral valve regurgitation, and also can be used to treat the tricuspid valve regurgitation, and also can be used in other minimally invasive surgeries (including operations besides the cardiac operation) that require clamping several pieces of tissues.

The present invention has the following beneficial technical effects:

(1) Minimally invasive implantation: The implantation of the valve clamp of the present invention does not need to open the chest. The valve clamp can be implanted through the apex cordis or peripheral artery. The wound is small. The cardiac arrest and extracorporeal circulation are not necessary. The implantation of the valve clamp belongs to the minimally invasive operation and can be used to treat patients in high-risk for traditional surgical techniques or patients with contraindications.

(2) The manufacture is simple and matured: The clamp of the present invention has a simple design. The manufacture method of the clamp is similar to the current common intravascular stent and the delivery system. Thus, the manufacture is relatively simple and mature.

(3) The difficulty of the procedure operation is low: One embodiment of the present invention can be accomplished through the apex cordis path, entering the left ventricle from the precordium to reach the valve directly. The entering location of the operation is near the valve. The access path of the sheath is straight and short. The delivery system does not need to turn around, facilitating the adjustment, control, and the surgical operation.

(4) The result is positive: The therapeutical effects of surgical edge-to-edge suture technique with respect to the mitral valve regurgitation have been proved definitely. The valve clamp of the present invention is designed based on the technical principle of the current surgical edge-to-edge suture. After the clamp is implanted, the two leaflets of the mitral valve are finally clamped, so as to achieve the same effect as that of the surgical edge-to-edge suture operation.

Hereinafter, with reference to the drawings, the concept of the present invention, the specific structure, and the produced technical effects are further described, so as to frilly illustrate the objectives, characteristics, and effects of the present invention.

BRIEF DESCRIPTION OF THE DRAWINGS

in FIG. 1, H1 is the superior vena cava, H2 is the inferior vena cava, H3 is the right atrium, H4 is the tricuspid valve, H5 is the right ventricle, H6 is the pulmonary valve, H7 is the pulmonary artery, H8 is the pulmonary vein, H9 is the left atrium, H10 is the mitral valve, H11 is the left ventricle, H12 is the aortic valve, H13 is the aorta, H14 is the descending aorta, H15 is the flow direction of oxygenated blood, and H16 is the flow direction of deoxygenated blood;

FIG. 2a and FIG. 2b are the schematic diagrams of the surgical edge-to-edge suture technique of mitral valve, wherein FIG. 2a is the scenario when the mitral valve is closed, and FIG. 2b is the scenario when the mitral valve is open;

FIG. 7a and FIG. 7b are schematic diagrams of the three-dimensional structures of the second clamp part of a preferred embodiment of the present invention;

DETAILED DESCRIPTION OF THE INVENTION

Figure 1:
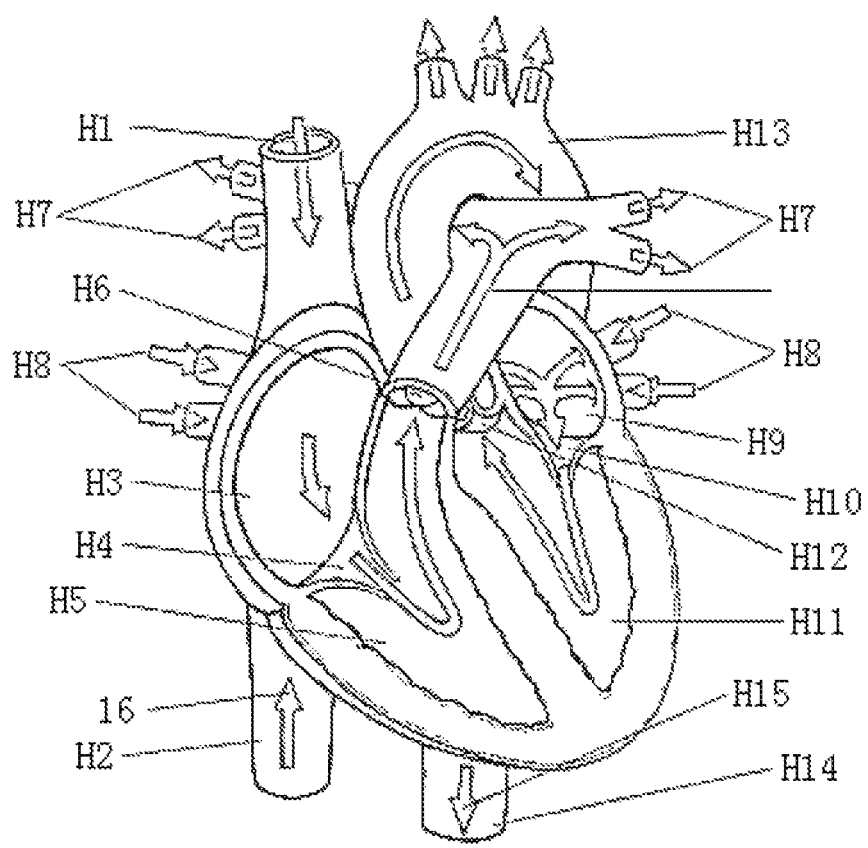
FIG. 1 is the schematic diagram of cardiac anatomic structure.
Figure 3:
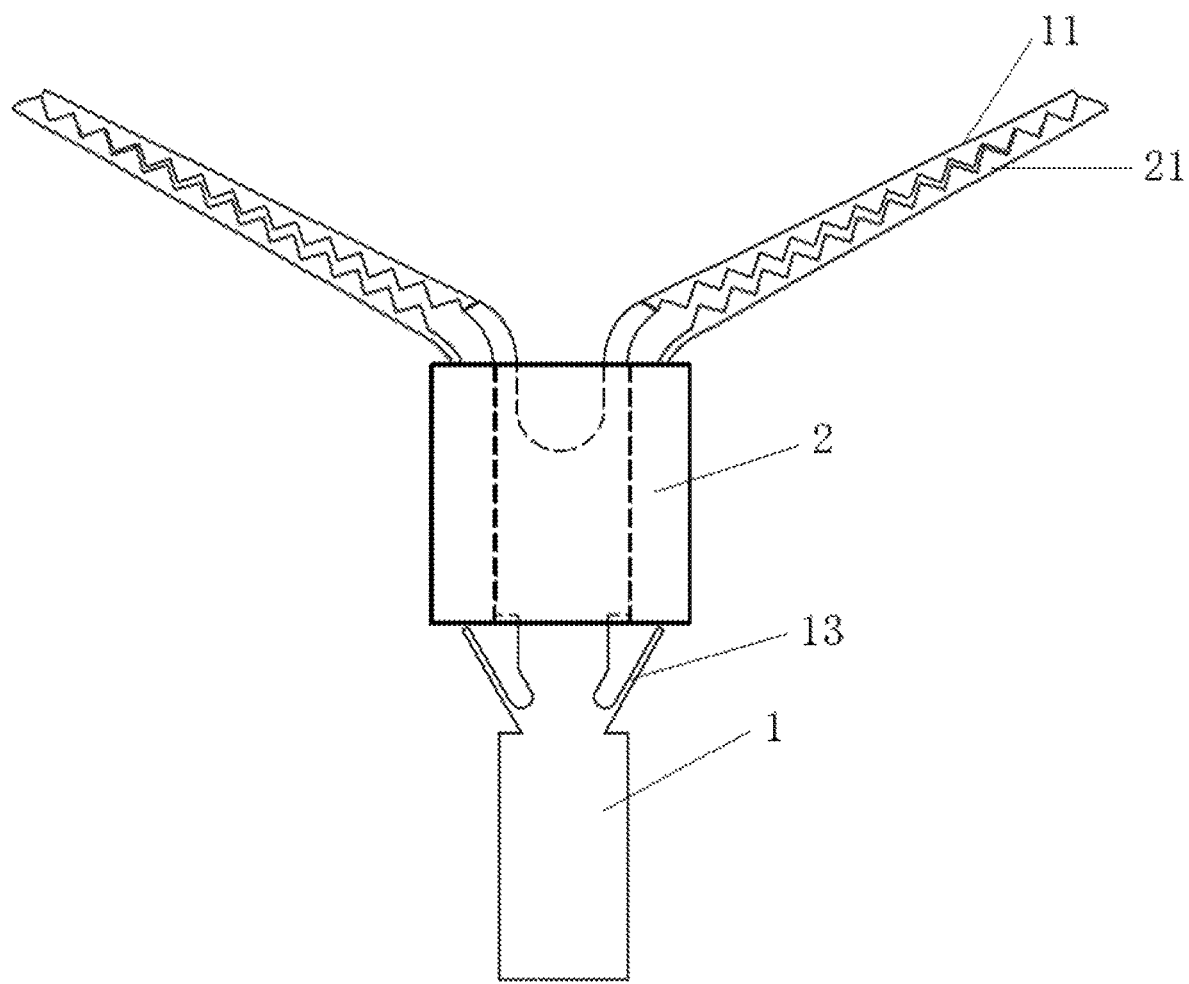
FIG. 3 is the schematic diagram combining the first clamp part and the second clamp part of a preferred embodiment of the present invention.
Figure 4:
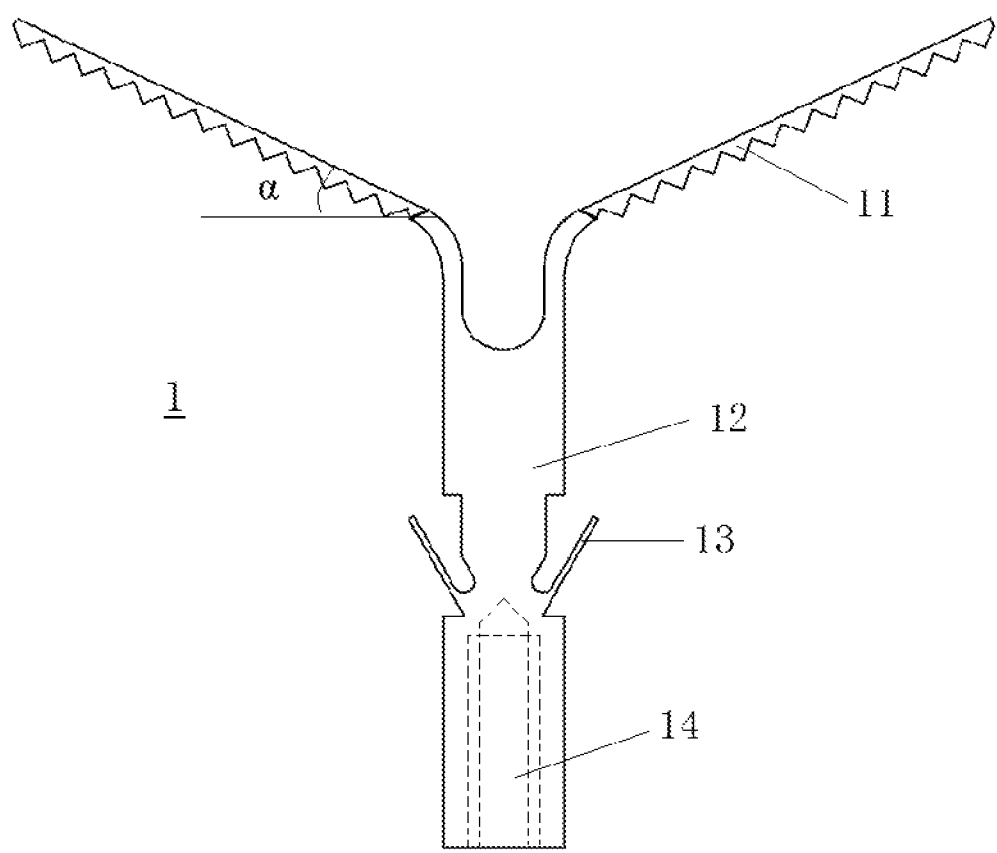
FIG. 4 is the schematic diagram of the structure of the first clamp part of a preferred embodiment of the present invention.
Figure 5:
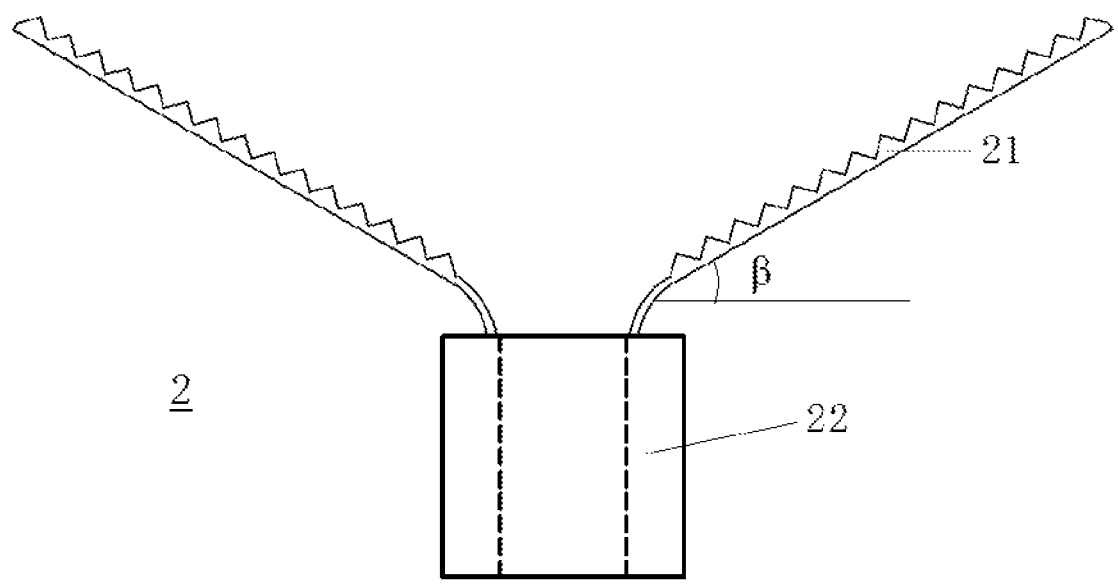
FIG. 5 is the schematic diagram of the structure of the second clamp part of a preferred embodiment of the present invention.

As shown in FIGS. 3-5 which are the schematic diagrams of the structure of a mitral valve clamp of the present invention, the valve clamp includes the first clamp part 1 and the second clamp part 2. The first clamp part includes a pair of V-shaped first clamping arms 11 and locking bar 12 which connects the pair of first clamping arms 11. The second clamp part includes a pair of V-shaped second clamping arms 21 and clamping ring 22 which connects the pair of second clamping arms 21. The locking bar 12 and clamping ring 22 can fit and be connected to each other, wherein the included angle of the two first clamping arms 11 is slightly more than the included angle of the two second clamping arms 21. In other words, the inclined angle α of the first clamping arm 11 is slightly less than the inclined angle β of the second clamping arm 21. The inclined angle α of the first clamping arm 11 refers to the included angle of the first clamping arm 11 and the line which is perpendicular to the direction of the axis of locking bar 12. The inclined angle β of the second clamping arm 21 refers to the included angle of the second clamping arm 21 and the line which is perpendicular to the direction of the axis of clamping ring 22. Preferably, α is 25°, and β 30°. The pair of first clamping arms 11 and the pair of second clamping arms 21 correspond to each other one by one. When they close, the force pushing against each other can be generated. Thus, two groups of clamps for clamping the mitral valve are formed. In other embodiments of the present invention, the first clamping arms can be provided on the clamping ring, and the second clamping arms can be provided on the locking bar, as long as the clamping principle of the present invention can be met.

In the present embodiment, locking bar 12 and clamping ring 22 are used as the connecting parts. Since, in the present embodiment, the connecting parts are respectively connected to the first clamping arms 11 and the second clamping arms 21 directly, in order to facilitate the description, the present embodiment defines locking bar 12 and clamping ring 22 as the constituent parts of the first clamp part 1 and the second clamp part 2 respectively. In other embodiments of the present invention, the locking bar and the clamping ring can also be associated with the first clamp part and the second clamp part via other structures.

Figures 6A, 6B:
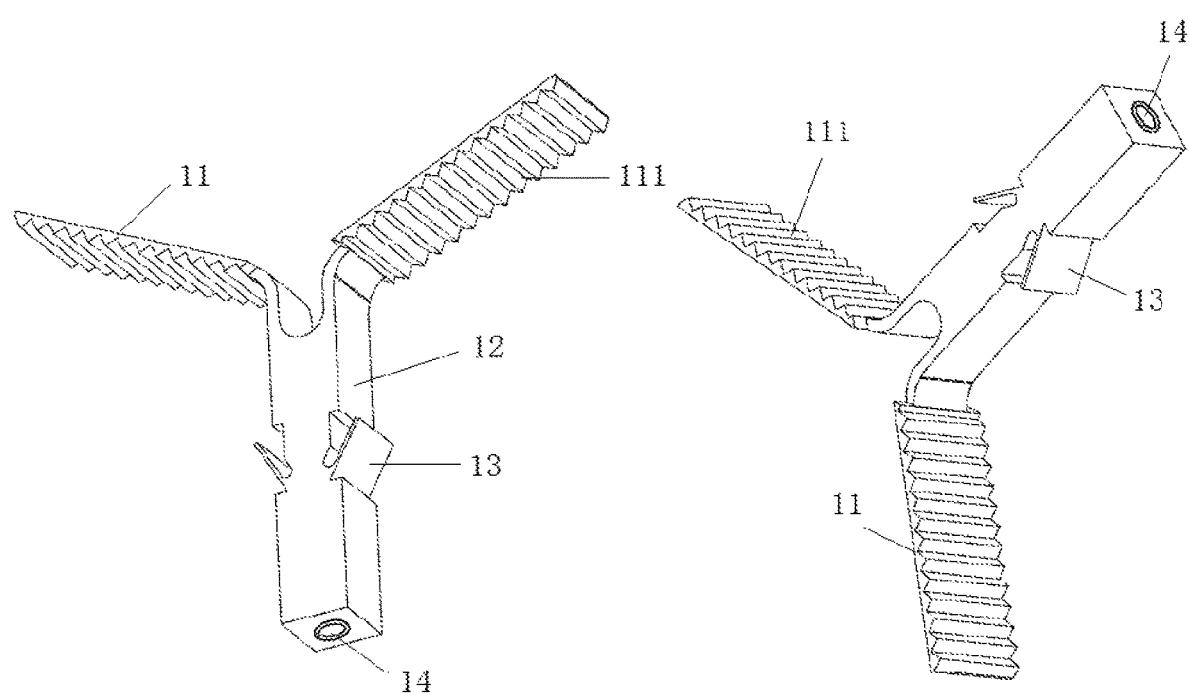
FIG. 6a and FIG. 6b are schematic diagrams of the three-dimensional structures of the first clamp part of a preferred embodiment of the present invention.

Referring to FIG. 6a and FIG. 7b respectively, it is shown that the lower surface of the first clamping arm 11 has zigzag projections 111. The upper surface of the second clamping arm 21 also has corresponding zigzag projections 211. Thus, the friction between the clamping arm and the valve tissue can be enhanced, preventing the clamped valve tissues from slipping out. In other embodiments of the present invention, the projections can also he wavy, thorny, etc.

The locking bar 12 has the shape of a square column. The clamping ring 22 is provided with ring hole 221 in the shape of a square column, which exactly fits the shape of locking bar 12, such that after locking bar 12 is inserted into clamping ring 22, rotating displacement or inclining will not occur. The locking bar 12 is also provided with elastic piece 13. The opening direction of the elastic piece is oriented toward the first clamping arm 11. The distance of the elastic piece from the fixed position of the first clamping arm 11 on locking bar 12 is larger than or equal to the axial length of clamping ring 22. During the assembly, it is only required to insert locking bar 12 into ring hole 221 of clamping ring 22 from the rear end. When elastic pieces 13 are passed through, elastic pieces 13 will close up. After elastic piece 13 are passed through, the two elastic pieces automatically pop out to snap fit clamping ring 22, such that the relative position of the elastic pieces with respect to locking bar 12 is locked. The locked position also determines the clamping status of the first clamping arms 11 and the second clamping arms 21. Elastic pieces 13, as the locking part, can be made of elastic high polymer material or elastic metal material. In other embodiments of the present invention, the locking part can also be a spring convex button, or snap-in parts in other forms.

Furthermore, the rear end (the lower end in the drawings) of the locking bar 12 is also provided with connecting port 14, which is used to connect the delivery device. The connecting manner can be a threaded connection.

Figure 8:
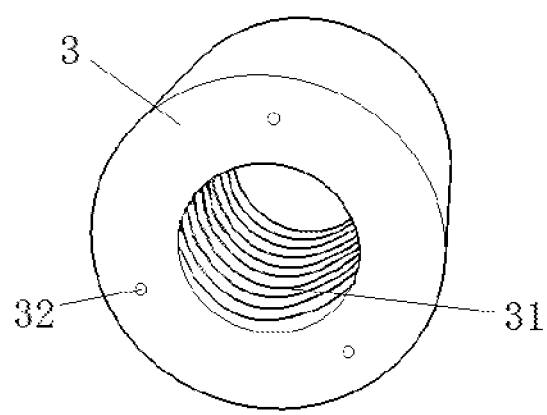
FIG. 8 is the schematic diagram of the three-dimensional structure of the closed ring of a preferred embodiment of the present invention.

The valve clamp of the present embodiment also includes closed ring 3 (as shown in FIG. 8), which has internal thread 31 and three small holes 32. Meanwhile, the outer surface of clamping ring 22 in the present embodiment has external thread 222 (as shown in FIGS. 7a and 7b). Clamping ring 22 can be screwed in or out of the closed ring 3 if necessary. In order to screw in or out the clamping ring nicely, the two second clamping arms 21 are provided near the outer edge of the plane at the front end of the clamping ring 22. After clamping ring 22 is screwed in completely, the closed ring 3 can play the role of closing up the first clamping arms and the second clamping arms toward the central line, thereby further improving the capability of clipping the valve tissues by the clamping arms, and closing up the clamped valve tissues toward the middle. The extent of closing up can be adjusted by adjusting the relative position of the closed ring 3 with respect to clamping ring 22. The three small holes 32 on the rear end of the closed ring 3 are used to receive the nails on the delivery pipe, such that the delivery pipe is connected flexibly.

Figure 9:
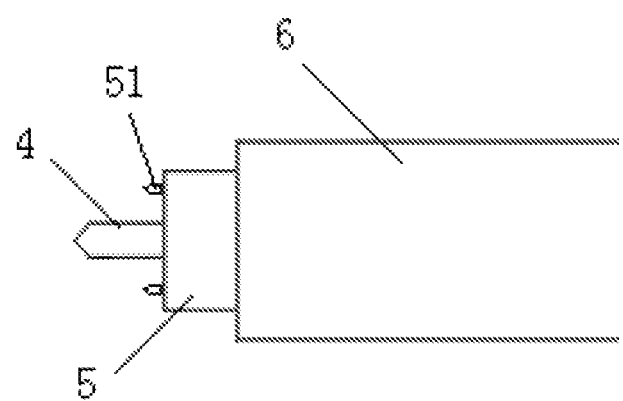
FIG. 9 is the schematic diagram of the three-layer structure of the delivery device.

FIG. 9 shows the schematic diagram of the structure of the delivery device of the present embodiment. The delivery device includes delivery rod 4, delivery pipe 5, and delivery sheath 6. Their rear ends can be pushed, pulled, rotated by the surgical operator. Delivery rod 4 is used to connect to locking bar 12 of the first clamp part 1. The front end of the delivery rod can be provided with the external threads, which are used to fit connecting port 14. The front end of delivery pipe 5 is provided with three nails 51, which fit the three small holes 32 on the rear end of closed ring 3. Nails 51 can be inserted into small holes 32, combining closed ring 3 and delivery pipe 4. When delivery pipe 4 is driven forward or rotates, closed ring 3 will move forward or rotate accordingly. When delivery pipe 4 moves backward, the closed ring 3 and the delivery pipe 4 will be separated. In order to reinforce the combination of the closed ring 3 and the delivery pipe 4, a suture line can be provided therebetween. The suture line can extend outside the body. When the clamping reaches a satisfied working state, the suture line can be cut off outside the body, such that the closed ring and the delivery pipe can be separated. Delivery sheath 6 provides a trail for the delivery. By pushing delivery rod 4 and delivery pipe 5, clamping arms can travel inside the delivery sheath, so as to enter the heart from outside the body. The delivery sheath can also protect the body tissue from being hurt by the clamping arms.

The valve clamp has three forms, i.e., the first form of completely radially contracting, the second form of completely radially expanding, and the third form of half contracting and half expanding (under the clamping status) respectively. The first form is the one in which the clamp is delivered through the catheter, i.e., the form in which the first clamping arms 11 and the second clamping arms 21 are both accommodated inside delivery sheath 6. The second form is the one in which the clamp is released from delivery sheath 6. At this time, the first clamping arms 11 and the second clamping arms 21 both stretch out completely. Moreover, the first clamping arms 11 and the second clamping arms 21 can be positioned at both sides of the valve respectively, getting ready for the next step of clamping. The third form is the working form after the clamp clamps the valve tissues, i.e., the form in which the positions of clamping ring 22 and closed ring 3 are fixed after clamping ring 22 is screwed into closed ring 3.

The preferred use path of the valve clamp is apex cordis puncture. The valve clamp enters the left ventricle from the precordium to directly reach the valve. The entry location of the operation is near the valve. The entry path of the sheath is straight and short. The delivery system does not need to turn around, facilitating the adjusting, the controlling, and the surgical operation.

The valve clamp of the present embodiment uses the technologies of laser cutting and engraving. However, the manufacturing method is not unique. In other preferred embodiments, the valve clamp can also be made by 3D printing technology integrally. The basic material of the present embodiment is the common Ni—Ti alloy. The delivery pipe, the delivery sheath, and the closed ring are made of a common material such as polyethylene and so on. The delivery rod is made of stainless steel.

The valve clamp of the present embodiment can use the following steps during the actual implantation:

1) Outside the body, the first clamp part of the clamp passes through the second clamp part, and is connected to the delivery rod. The delivery rod is located inside the delivery pipe. The second clamp part is connected to the delivery pipe. The delivery pipe is located inside the delivery sheath. Finally, the first clamp part and the second clamp part are both loaded inside the delivery sheath.

2) The delivery sheath is fed into the left ventricle tube, passing through the orifice of the mitral valve to reach the left atrium. The delivery sheath is drawn back, such that the first clamp part leaves the delivery sheath and stretches inside the left atrium.

3) The delivery sheath is further drawn back to the left ventricle, such that the second clamp part leaves the delivery sheath and stretches inside the left ventricle.

4) The second clamp part is pushed upward, pushing the leaflets of the mitral valve to the left atrium, reducing the activities of the mitral valve leaflets. The first clamp part is pulled downward, such that after the elastic pieces pass through the ring hole of the clamping ring, two groups of clamping arms are combined together firmly to form the clamps. The two groups of clamps will dip the two leaflets of the mitral valve.

5) The delivery sheath is pushed upward, retracting the two groups of clamps into the delivery sheath. The closed ring is driven to rotate by rotating the delivery pipe. The two groups of clamps are retracted into the closed ring, such that they are closed toward the central line.

6) The delivery sheath is drawn back, the delivery rod is screwed out of the delivery sheath, and the closed ring is separated from the delivery pipe, finally releasing the clamp. The operation is completed, leaving the clamp inside the body, clamping the leaflets of the mitral valve.

Hereinabove, the preferred embodiments of the present invention are described in detail. It should be understood that a person of ordinary skill in the art can make various modifications and changes based on the concept of the present invention without creative efforts. Thus, the technical solutions obtained by the person of ordinary skill in the art, on the basis of the prior art according to the concept of the present invention through logic analysis, inference, or finite experiments, all fall within the protective scope defined by the claims.

What is claimed is:

1. A valve clamp, comprising:
   a first clamp part,
   a second clamp part and
   a connecting part;
   wherein
   the first clamp part includes at least two first clamping arms;
   the second clamp part includes second clamping arms corresponding to the first clamping arms;
   each first clamping arm and each corresponding second clamping an form a group of clamp;
   each first clamping arm and each corresponding second clamping arm clip an object therebetween through an interaction force generated by closing up and pushing against each other; and
   the connecting part is used to connect the first clamp part and the second clamp part wherein the first clamping arms inclines toward a front of the clamp; the second clamping arms also inclines toward the front of the clamp; and an inclined angle of the second clamping arms is more than an inclined angle of the first clamping arms; wherein the connecting part includes a locking bar and a clamping ring fitting each other; the first clamp part and the second clamp part are respectively connected to the locking bar or the clamping ring; the locking bar is inserted into a ring hole of the clamping ring to connect the first clamp part and the second clamp part; and a locking part is further provided between the locking bar and the clamping ring.

2. The valve clamp according to claim 1, wherein an inclined angle of the first clamping arm is 20-30°; and an inclined angle of the second clamping arm is 25-35°.

3. The valve clamp according to claim 1, wherein a surface of the first clamping arms and an opposite surface of the second clamping arms both have a plurality of projections.

4. The valve clamp according to claim 1, wherein the valve clamp has three first clamping arms.

5. The valve clamp according to claim 1, wherein
the connecting part includes a locking bar and a clamping ring fitting each other;
the first clamp part and the second clamp part are respectively connected to the locking bar or the clamping ring;
the locking bar is inserted into a ring hole of the clamping ring to connect the first clamp part and the second clamp part; and
a locking part is further provided between the locking bar and the clamping ring.

6. The valve clamp according to claim 5, wherein
the locking bar is in a shape of a square column; and
the ring hole of the clamping ring is a corresponding hole with the shape of the square column.

7. The valve clamp according to claim 5, wherein
the locking part is provided on the locking bar, and
the locking part is an elastic piece.

\* \* \* \* \*